United States Patent
Orosz et al.

(10) Patent No.: US 9,000,206 B2
(45) Date of Patent: Apr. 7, 2015

(54) PROCESS FOR PREPARING TRIORGANO BORATES WITH LOW ALCOHOL CONTENT

(75) Inventors: Ronald J. Orosz, Cranberry Township, PA (US); David F. Rouda, Renfrew, PA (US); Karl Matos, Sewickly, PA (US)

(73) Assignee: BASF SE, Ludwigshafen (DE)

( * ) Notice: Subject to any disclaimer, the term of this patent is extended or adjusted under 35 U.S.C. 154(b) by 188 days.

(21) Appl. No.: 13/580,445

(22) PCT Filed: Feb. 16, 2011

(86) PCT No.: PCT/IB2011/050635
§ 371 (c)(1),
(2), (4) Date: Aug. 22, 2012

(87) PCT Pub. No.: WO2011/104653
PCT Pub. Date: Sep. 1, 2011

(65) Prior Publication Data
US 2012/0316364 A1    Dec. 13, 2012

Related U.S. Application Data

(60) Provisional application No. 61/308,328, filed on Feb. 26, 2010.

(51) Int. Cl.
*C07F 5/04* (2006.01)
(52) U.S. Cl.
CPC ........................................ *C07F 5/04* (2013.01)
(58) Field of Classification Search
CPC ............................ C10M 2227/061; C07F 5/04
USPC ...................... 568/6; 558/286, 296
See application file for complete search history.

(56) References Cited

U.S. PATENT DOCUMENTS

| | | | |
|---|---|---|---|
| 3,004,058 A | 10/1961 | Cunningham | |
| 3,005,011 A | 10/1961 | Bohm et al. | |
| 3,024,264 A * | 3/1962 | Petterson | 558/296 |
| 6,100,415 A | 8/2000 | Takamatsu et al. | |
| 7,932,329 B2 * | 4/2011 | Ito et al. | 526/77 |

FOREIGN PATENT DOCUMENTS

DE    3126111 A1    1/1983

OTHER PUBLICATIONS

Andersen, et al., E- and Z-Pentenylboronates, Reagents for Simple Diastereoselection on Addition to Aldehydes, Chem. Ber. 122 (1989) pp. 1777-1782.
Bowie, et al., "Organoboron Compounds, Part X. The Reaction of Lithium with Trialkyl Borates" Journal of the Chemical Society (C), 1970, pp. 2228-2229.
Hoffmann, et al., "Synthesis of 2,6-Dideoxy-L-hexoses" Liebigs Ann. Chem. (1987) pp. 881-886.
International Preliminary Report on Patentability for PCT/IB2011/050635, Jul. 14, 2011.
Lin, et al. "Enantioselective Synthesis of Janus Kinase Inhibitor INCB018424 via an Organocatalytic Aza-Michael Reaction" Organic Letters (2009) vol. 11, No. 9, pp. 1999-2002.
Mehrotra, et al. "Organic Derivatives of Boron. Part V.1 Pinacol Derivatives" Journal of the Chemical Society (1962) pp. 3819-3821.
Smoum, et al., Bioorganic Chemistry, 31 (2003) pp. 464-474.
International Search Report for PCT/IB2011/050635 mailed Jul. 14, 2011.

* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

The present invention provides a process for preparing triorgano borates with low alcohol content.

8 Claims, No Drawings

PROCESS FOR PREPARING TRIORGANO BORATES WITH LOW ALCOHOL CONTENT

RELATED APPLICATIONS

This application is a national stage application (under 35 U.S.C. §371) of PCT/IB2011/050635, filed Feb. 16, 2011, which claims benefit of U.S. Provisional Application No. 61/308,328, filed Feb. 26, 2010.

DESCRIPTION

The present invention relates to a process for preparing triorgano borates with low alcohol content.

Triorgano borates such as trimethylborate, triisopropylborate or isopropylpinacol borate are known to contain small amounts (up to 2 wt %) of the corresponding alcohol from which they were made (Mehrotra, R. C.; Srivastava, G., Journal of the Chemical Society 1962, pages 3819 to 21). Low levels of alcohol come from the manufacturing process where typically an alcohol is reacted with boric oxide ($B_2O_3$) or another borate followed by a distillation process. Known methods to remove residual alcohol from borates include azeotropic distillation using benzene, toluene or hexanes (Hoffmann, R. W.; Metternich, R.; Lanz, J. W., Liebigs Annalen der Chemie 1987, Vol. 10, pages 881 to 887; Andersen, M.; Hildebrandt, B.; Koester, G.; Hoffmann, R. W., Chemische Berichte 1989, Vol. 122, pages1777 to 1782; Smoum, R.; Rubinstein, A.; Srebnik, M., Bioorganic Chemistry 2003, Vol. 31, pages 464 to 474; Lin, Q.; Meloni, D.; Pan, Y.; Xia, M.; Rodgers, J.; Shepard, S.; Li, M.; Galya, L.; Metcalf, B.; Yue, T.-N.; Liu, P.; Zhou, J., Organic Letters 2009, Vol. 11, pages 1999 to 2002). However, complete removal of the alcohol to below 0.05 wt % levels is difficult to achieve by azeotropic distillation.

Many solvents can be dried by distillation over alkali metals, and also alcohol impurities can be removed that way. However, tralkyl borates are known to react with metals like lithium (Bowie, R. A., Musgrave, O. C., Goldschmid, H. R., J. Chem. Coc.© 1970, pages 2228 to 2229), magnesium, calcium, strontium or barium (Wiberg, E. et al., Z. Naturforschung 1955, Vol. 10b, page 290).

Triorgano borates are typically used in borylation reactions and in reactions with organometallic compounds like Grignard compounds, alkyllithiums, etc. Borylation reactions are common in the synthesis of pharmaceutical drugs. The products of such reactions are typically used in Suzuki cross-coupling reactions to prepare complex intermediates for pharmaceutical products. Presence of alcohols in the borate raw material may impair the reaction of borates with organometallic compounds because they will decompose the organometallic species, thus resulting in side products or lower yield. Syntheses of pharmaceuticals may be very costly and any yield loss resulting from alcohol presence in borates is undesired.

It was therefore an object of the present invention to develop a process for preparing triorgano borates with low alcohol content.

Accordingly, a process for preparing triorgano borates with low alcohol content was found, comprising the step of bringing a triorgano borate into contact with at least one alkali metal at temperatures below 150° C.

A preferred embodiment of the present invention is a process for preparing triorgano borates with low alcohol content, comprising the step of bringing a triorgano borate into contact with sodium-potassium-alloy at a temperature between 0 and 35° C., most preferred at ambient temperature.

In a preferred embodiment of the present invention the triorgano borate is brought into contact with at least one alkali metal for a period of between 1 and 12 hours.

In another preferred embodiment of the present invention the triorgano borate is distilled off from the reaction mixture after it was in contact with the at least one alkali metal according to the invention.

Examples for alkali metals are lithium, sodium, potassium, rubidium and cesium.

As used in connection with the present invention, the term triorgano borate denotes a compound of the general formula $$B(OR^1)(OR^2)(OR^3)$$

wherein $R^1$, $R^2$ and $R^3$ are the same or different organyl groups. Two of the groups $R^1$, $R^2$ and $R^3$ can also be connected to form a divalent organyl group (e. g. ortho-$C_6H_4$), that forms together with the $BO_2$ moiety, a cyclic structure.

Organyl groups as used herein are, for example, $C_1$-$C_{10}$ alkyl, $C_3$-$C_{10}$ cycloalkyl, $C_6$-$C_{14}$ aryl, $C_7$-$C_{16}$ aralkyl or $C_7$-$C_{16}$ alkaryl groups.

As used herein, the term "$C_1$-$C_{10}$ alkyl" denotes a branched or an unbranched saturated hydrocarbon group comprising between 1 and 10 carbon atoms. Examples are methyl, ethyl, propyl, isopropyl, n-butyl, isobutyl, sec-butyl, tert-butyl, amyl, isoamyl, sec-amyl, 1,2-dimethylpropyl, 1,1-dimethylpropyl, n-hexyl, 4-methylpentyl, 1-methylpentyl, 2-methylpentyl, 3- methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, n-heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 2-ethylhexyl, n-octyl, 6-methylheptyl, 1-methylheptyl, 1,1,3,3-tetramethylbutyl, n-nonyl, 1-, 2-, 3-, 4-, 5-, 6- or 7-methyloctyl, 1-, 2-, 3-, 4- or 5-ethylheptyl, 1-, 2- or 3-propylhexyl, n-decyl, 1-, 2-, 3-, 4-, 5-, 6-, 7- and 8-methylnonyl, 1-, 2-, 3-, 4-, 5- or 6-ethyloctyl and 1-, 2-, 3- or 4-propylheptyl. Preferred are the alkyl groups methyl, ethyl, propyl, isopropyl, n-butyl, isobutyl, sec-butyl, tert-butyl, amyl, isoamyl, sec-amyl, 1,2-dimethylpropyl and 1,1-dimethylpropyl, most preferred are isoamyl groups.

The term "isoamyl" denotes a branched methylbutyl group, preferably 3-methyl-2-butyl.

The term "$C_3$-$C_{10}$ cycloalkyl" denotes a saturated hydrocarbon group comprising between 3 and 10 carbon atoms including a mono- or polycyclic structural moiety. Examples are cyclopropyl, cyclobutyl, cyclopentyl, cyclohexyl, methylcyclohexyl, dimethylcyclohexyl, cycloheptyl, cyclooctyl, norbornyl, isopinocampheyl, cyclononyl or cyclodecyl. Preferred are the cycloalkyl groups cyclopentyl, cyclohexyl, methylcyclohexyl and isopinocampheyl.

The term "isopinocampheyl" denotes all stereoisomers of a bicyclic hydrocarbon group obtainable via hydroboration of a-pinene.

The term "$C_6$-$C_{14}$ aryl" denotes an unsaturated hydrocarbon group comprising between 6 and 14 carbon atoms including at least one aromatic ring system like phenyl or naphthyl or any other aromatic ring system. ortho-$C_6H_4$ denotes a divalent aryl group occurring in catechol-type derivatives.

The term "$C_7$-$C_{16}$ aralkyl" denotes an aryl-substituted alkyl group comprising between 7 and 16 carbon atoms including for example a phenyl-, naphthyl- or alkyl-substituted phenyl- or alkyl-substituted naphthyl-group or any other aromatic ring system. Examples of aralkyl groups include benzyl, 1- or 2-phenylethyl, 1-, 2- or 3-phenylpropyl, mesityl and 2-, 3- or 4-methylbenzyl groups.

The term "$C_7$-$C_{16}$ alkaryl" denotes an alkyl-substituted aryl group comprising between 7 and 16 carbon atoms including for example a phenyl- or naphthyl- or alkyl-substituted phenyl- or alkyl-substituted naphthyl-group or any other aromatic ring system and an alkyl substituent as defined above. Examples for alkaryl groups are 2,- 3- or 4-methylphenyl, 2,- 3- or 4-ethylphenyl and 2,- 3-, 4-, 5-, 6-, 7- or 8-methyl-1-naphthyl groups.

The new process according to the invention allows for the preparation of triorgano borates with residual alcohol contents of below 0.1 wt %.

Therefore, another embodiment of the present invention is a triorgano borate with an alcohol content of below 0.1 wt %.

EXAMPLE 3.5 g of sodium-potassium-alloy and 279 g isopropylpinacol borate (1.5 moles, containing 0.226 wt % of isopropanol) were stirred under nitrogen atmosphere at room temperature for 1 hour. Samples were taken and monitored by $^{11}$B NMR spectroscopy. During a period of 3 hours an increase of the corresponding "ate" complex was noted (0.19 to 0.27%). The majority of the content was distilled into an oven dried clean distillation receiver (103° C., 65 mmHg). The final product was analyzed by GC to find that the distillate only contained 0.057 wt % of isopropanol.

The invention claimed is:

1. A process for preparing triorgano borates with an alcohol content of below 0.1 wt %, comprising the step of bringing a triorgano borate into contact with at least one alkali metal at temperatures below 150° C.

2. A process according to claim 1, comprising the step of bringing a triorgano borate into contact with sodium-potassium-alloy at a temperature between 0 and 35° C.

3. A process according to claim 1, comprising further the step of distilling out the triorgano borate.

4. A triorgano borate with an alcohol content of below 0.1 wt %.

5. A process according to claim 2, comprising further the step of distilling out the triorgano borate.

6. A process according to claim 1, wherein the triorgano borate is brought into contact with at least one alkali metal for a period of between 1 and 12 hours.

7. A process according to claim 1, wherein said at least one alkali metal is lithium, sodium, potassium, rubidium or cesium.

8. A process according to claim 1, wherein said triorgano borate is a compound of the formula $$B(OR^1)(OR^2)(OR^3)$$

wherein $R^1$, $R^2$ and $R^3$ are the same or different organyl groups or wherein two of the groups $R^1$, $R^2$ and $R^3$ can also be connected to form a divalent organyl group that forms together with the $BO_2$ moiety, a cyclic structure.

* * * * *